United States Patent [19]

Weymouth, Jr. et al.

[11] Patent Number: 4,964,714
[45] Date of Patent: Oct. 23, 1990

[54] SAFETY SPECTACLES AND TEMPLE THEREFOR

[75] Inventors: Russell F. Weymouth, Jr., Charlton Depot, Mass.; John J. McNamara, Scranton; Joseph A. Cianflone, Carbondale, both of Pa.

[73] Assignee: Gentex Corporation, Carbondale, Pa.

[21] Appl. No.: 428,038

[22] Filed: Oct. 26, 1989

Related U.S. Application Data

[63] Continuation of Ser. No. 220,792, Jul. 14, 1988, abandoned.

[51] Int. Cl.⁵ .................. G02C 11/08; G02C 5/14; A61F 9/02
[52] U.S. Cl. .................. 351/62; 351/111; 2/436
[58] Field of Search .......... 351/111, 62, 153, 121; 2/439, 436, 437

[56] References Cited

U.S. PATENT DOCUMENTS

| 2,288,423 | 6/1942 | Root | 2/436 |
| 3,497,294 | 2/1970 | Volk | 351/62 |
| 4,271,538 | 6/1981 | Montesi et al. | 2/439 |
| 4,425,669 | 1/1984 | Grendol | 2/436 |
| 4,605,293 | 8/1986 | Blumenthal | 351/121 X |
| 4,832,479 | 5/1989 | Beyer et al. | 351/121 |

Primary Examiner—Rodney B. Bovernick
Attorney, Agent, or Firm—Shenier & O'Connor

[57] ABSTRACT

Safety spectacles comprising a front and pivotally attached temples adapted to extend rearwardly from the front. Each temple has a portion recessed inwardly relative to an adjacent portion of the front to form a passage to the region behind the front for ventilation. The recessed temple portions extend forwardly of the rear edges of the front so as to overlap the adjacent portions of the front and thereby increase the degree of protection to the wearer.

9 Claims, 3 Drawing Sheets

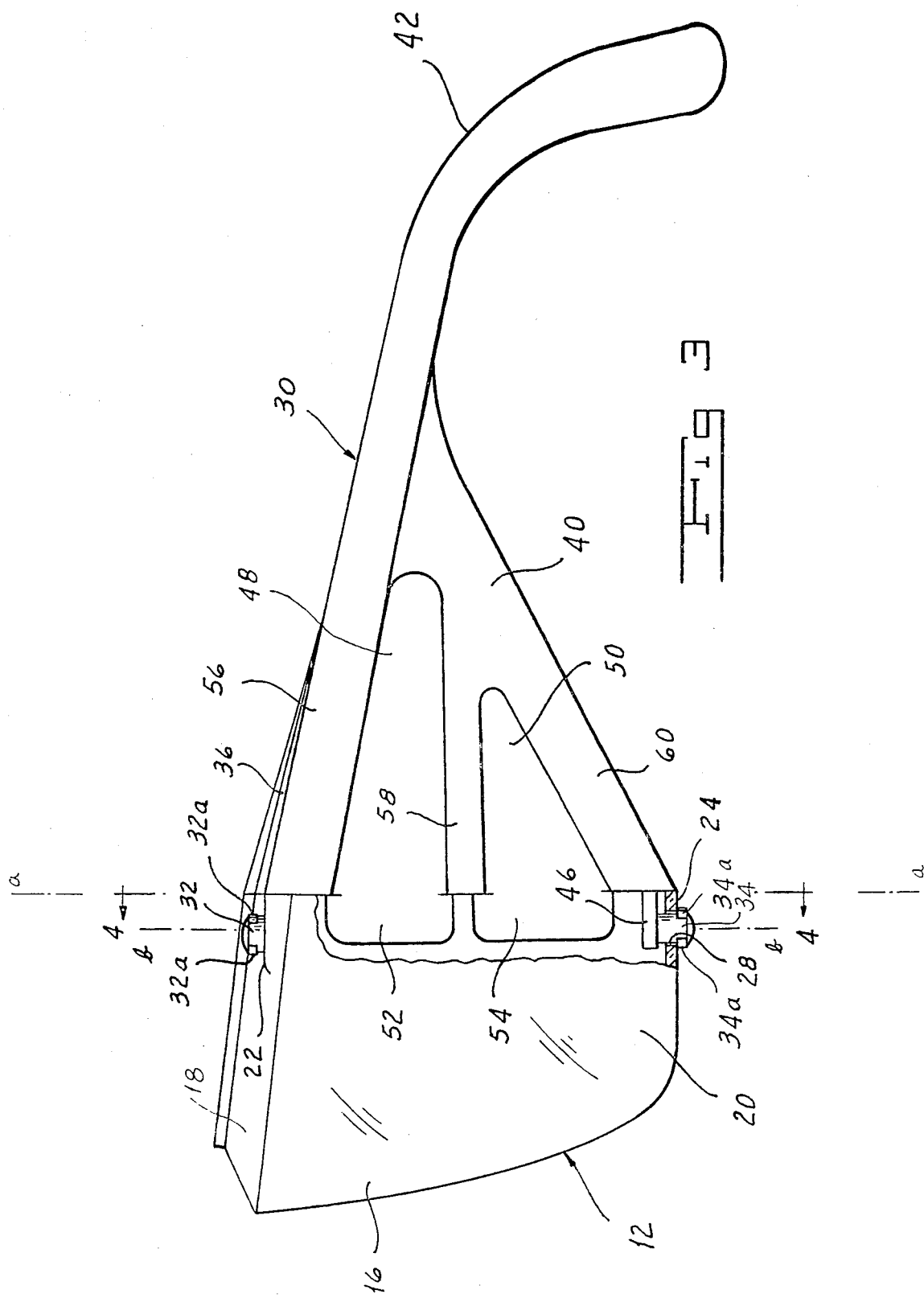

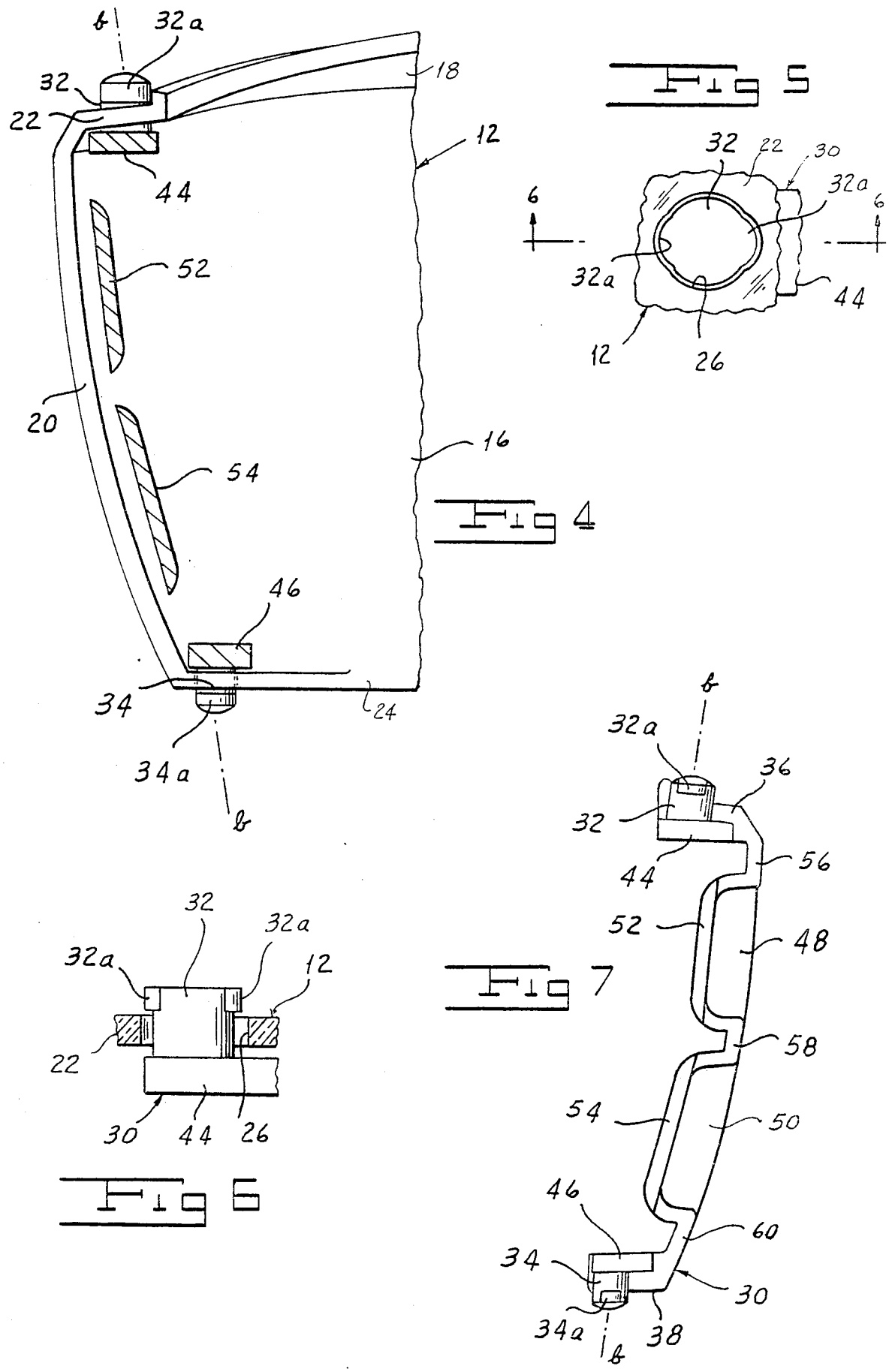

SAFETY SPECTACLES AND TEMPLE THEREFOR

This is a continuation of copending application Ser. No. 07/220,792 filed on July 14, 1988 now abandoned.

FIELD OF THE INVENTION

This application relates to a pair of safety spectacles for use in industrial or other applications requiring protection of the eyes and adjacent facial portions against injury from projectiles or other hazards.

BACKGROUND OF THE INVENTION

U.S. Pat. No. 4,271,538, issued to Edward N. Montesi et al, discloses a pair of safety spectacles having a one-piece front or facepiece shaped to wrap around the wearer's eyes and having temples pivotally attached thereto. The one-piece front includes a central optical portion of the "mono lens" type having a single optical axis and a corrected optical curve for zero refractive power. The front and the temples each include inwardly projecting upper and lower flanges to enclose the region between the spectacles and the wearer's face and thereby increase the degree of protection. Owing to such enclosure, however, the rear surface of the front is relatively poorly ventilated and is thus susceptible to fogging.

The patent specification teaches that the temples may be provided with air vents of various types, and specifically discloses the use of louvers for providing desired ventilation. The disclosed louvers are angled so as to direct air inwardly and forwardly against the rear surface of the one-piece front. Owing to the practicalities of mold design, however, the louvers do not overlap, as viewed from the side, creating the possibility for injury to the eyes or face from projectiles or the like. Further, the louvers have a relatively small extent in the direction of the airflow, and hence cannot efficiently direct air against the rear surface of the lens front.

SUMMARY OF THE INVENTION

One object of our invention is to provide a pair of safety spectacles that adequately protect the wearer from injury.

Another object of our invention is to provide a pair of safety spectacles that afford adequate ventilation and resist fogging.

Still another object of our invention is to provide a pair of safety spectacles that are simple and inexpensive to manufacture.

Other and further objects will be apparent from the following description.

In general, our invention contemplates safety spectacles comprising a front and a pair of temples adapted to extend rearwardly from the front in which each temple has a portion recessed inwardly relative to an adjacent portion of the front to form a passage to the region behind the front. Our invention also contemplates the temples themselves as separate articles of manufacture for use with suitably designed fronts. Preferably, the temples are separately formed members pivotally attached to the front, while the recessed portions extend forwardly of the rear edges so as to overlap adjacent portions of the front. Each temple preferably has a plurality of vertically spaced recessed portions as well as unrecessed portions adapted to mate with the adjacent portions of the front.

By recessing portions of the temples inwardly relative to adjacent portions of the front, we provide ventilating passages to the region between the front and the wearer's eyes without the necessity of louvers or the like and their attendant disadvantages. Further, by overlapping the recessed temple portions and the adjacent portions of the front, we direct the airflow to the rear surface of the front, where it is desired, while shielding the wearer's eyes from injury. At the same time, the unrecessed temple portions continue to function as limit stops, limiting the outward pivotal movement in a manner similar to that of the existing spectacles referred to above.

BRIEF DESCRIPTION OF THE DRAWINGS

In the accompanying drawings to which reference is made in the instant specification and which are to be read in conjunction therewith and in which like reference characters are used to indicate like parts in the various views:

FIG. 3 is an enlarged left elevation of the spectacles of FIG. 1, with parts broken away or shown in section.

FIG. 4 is an enlarged fragmentary section of the spectacles of FIG. 1 along line 4—4 of FIG. 3.

FIG. 5 is an enlarged fragmentary top plan of an upper hinge portion of the spectacles of FIG. 1.

FIG. 6 is a fragmentary section of the hinge portion shown in FIG. 5.

FIG. 7 is an enlarged front elevation of the left temple of the spectacles shown in FIG. 1.

DESCRIPTION OF THE PREFERRED EMBODIMENT

Figure 1:
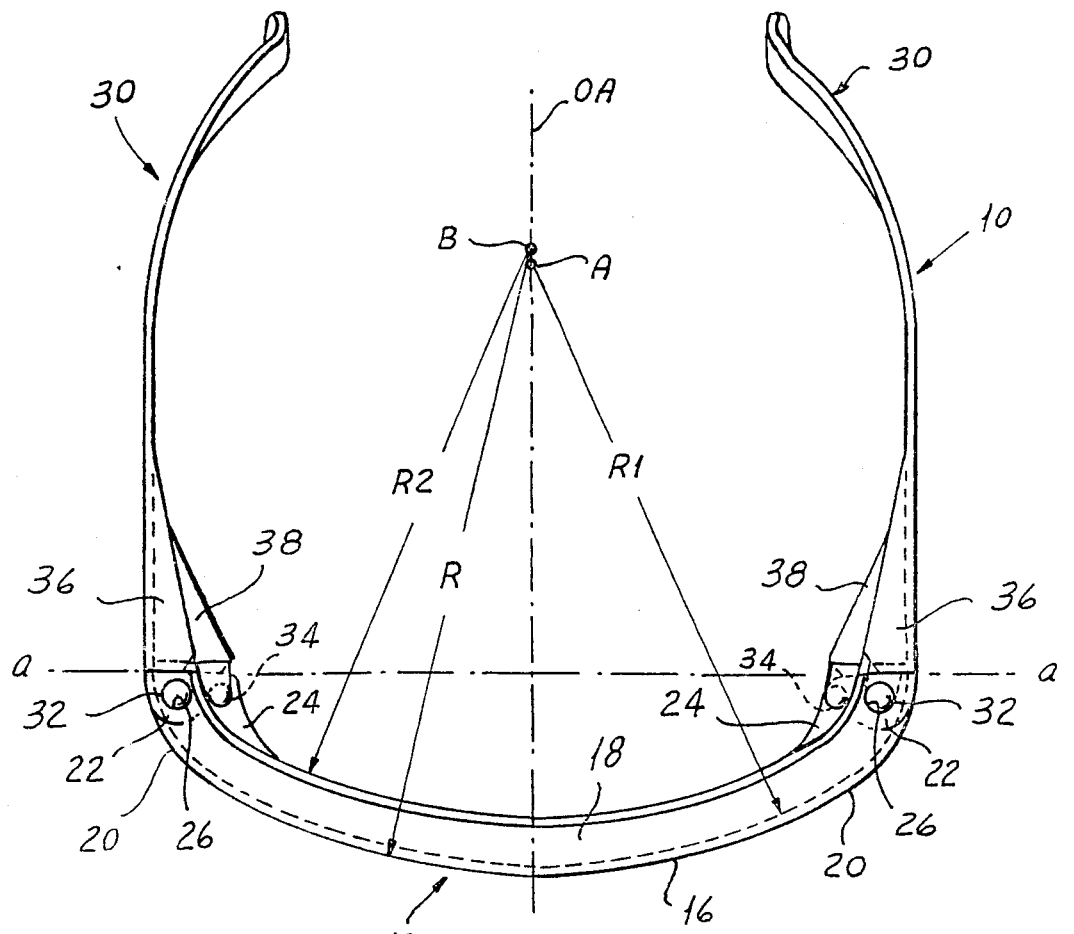
FIG. 1 is a top plan of a pair of safety spectacles constructed according to our invention.
Figure 2:
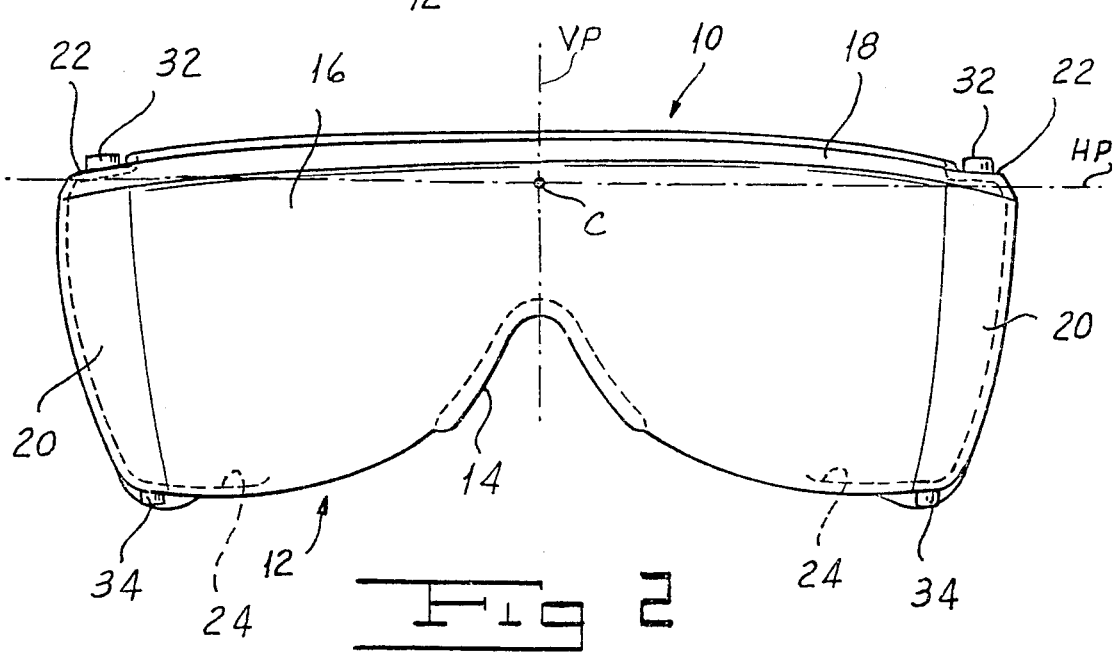
FIG. 2 is a front elevation of the spectacles of FIG. 1.

Referring first to FIGS. 1 to 3, a pair of safety spectacles constructed according to our invention, indicated generally by the reference numeral 10, include a facepiece or front, indicated generally by the reference numeral 12, to which are pivotally attached left and right temples indicated generally by the reference numeral 30. Front 12 is also shown in the above-identified U.S. Pat. No. 4,271,538 to Montesi et al, the specification of which is incorporated herein by reference. Front 12 and temples 30 preferably comprise a suitable transparent plastic such as polycarbonate. Front 12 has a curvature generally corresponding to that of the wearer's face, as shown in FIG. 1, and is formed with a rearwardly projecting nosepiece 14 (FIG. 2) for supporting the front 12 on the wearer's nose. Front 12 comprises a central optical portion 16 through which the wearer sees and side portions 20 constituting interfaces between the central portion 16 and temples 30. Side portions 20 of front 12 have rear edges (FIG. 4) located in a vertical plane a—a (FIG. 1) coincident with the sectional plane 4—4 shown in FIG. 3.

As shown in FIGS. 1 and 3, central portion 16 and side portions 20 of front 12 are formed with a rearwardly projecting flange 18 extending across the top of the front 12. Upper flange 18 merges into respective left and right upper flanges 22 of side portions 20, which side portions are formed along their lower edges with rearwardly projecting flanges 24. Upper flanges 22 have apertures 26, while lower flanges 24 have similarly shaped apertures 28. As shown in FIG. 5 for upper left aperture 26, each of apertures 26 and 28 comprises a bore formed with smaller-radius cutouts at diametrically opposite portions of its periphery for a purpose to be described.

As described in more detail in the above-identified patent of Montesi et al, central portion 16 of facepiece 12 is of the so-called "mono lens" design, having a single optical axis OA (FIG. 1) extending rearwardly from a point C (FIG. 2) along the vertical midline of the central portion 16 near the upper flange 18. Optical axis OA is formed by the intersection of a horizontal plane HP and a vertical plane VP (FIG. 2) containing point C. Central portion 16 of front 12 has a spherical front surface with a center of curvature A along the optical axis OA (FIG. 1) and a radius of curvature R, together with a spherical rear surface with a center of curvature B along the optical axis OA slightly behind point A and a radius of curvature R1. The rear edge of the upper flange 18 of central portion 16 has a center of curvature at point A, and a radius of curvature R2.

As disclosed in the above-identified U.S. Pat. No. 4,271,538, the radii R, R1 and R2 are preferably 5.033 inches (12.78 cm), 5 inches (12.7 cm) and 4.564 inches (11.6 cm), respectively. Further, point B is preferably located 0.057 inch (1.448 mm) behind point A, resulting in a lens thickness that is a maximum of 0.090 inch (2.286 mm) at the optical axis 0A and progressively decreases along the surface of the portion 16 in any direction from the point C on the optical axis OA. For a polycarbonate lens of 1.586 index of refraction, this corrected curvature results in a lens of zero refractive power for the radii and distances specified above. By contrast, if the front 12 had simply had a constant-thickness central optical portion 16, with coincident centers of curvature A and B for the front and rear surfaces, the resulting lens would have had a slight negative power of about 0.053 diopter.

Referring now to FIG. 3, each temple 30 comprises a generally triangular front portion 40, which shields the adjacent portion of the wearer's face, and a curved relatively narrow rear portion 42 adapted to extend over the wearer's ears. Referring also to FIGS. 1 and 7, front portion 40 of temple 30, which generally extends rearwardly from plane a—a, has an inwardly projecting upper flange 36 extending along the top as well as an inwardly projecting lower flange 38 extending along the bottom. Temple flanges 36 and 38 mate with flanges 22 and 24 of side portions 20 to enclose the region between front temple portion 40 and the wearer's temple as well as provide flexural rigidity. Respective upper and lower tabs 44 and 46 projecting forwardly of plane a—a from flanges 36 and 38 of temple 30 support respective upper and lower pins 32 and 34. Pins 32 and 34 extend through respective apertures 26 and 28 to support the temple 30 for pivotal movement relative to front 12. Left temple 30 pivots on an axis b—b (FIGS. 4 and 7) which is inclined from the vertical by an angle of about 8.5°, with the upper pin 32 being farthest from the vertical plane VP (FIG. 2). Right temple 30 has a similarly inclined pivot axis, in mirror-image fashion.

As shown in FIGS. 5 and 6 for upper pin 32, pins 32 and 34 are generally cylindrical but have retainer portions 32a and 34a at diametrically opposite locations on the pins at the ends remote from the supporting tabs 44 and 46. Portions 32a and 34a are rounded in a manner corresponding to that of the cutouts of apertures 26 and 28. Temples 30 are attached to front 12 by flexing the temples slightly and inserting pins 32 and 34 into apertures 26 and 28 with tabs 32a and 34a in alignment with the cutouts in apertures 26 or 28 as shown in FIGS. 5 and 6 for upper pin 32. To remove temples 30 from front 12, the reverse procedure is used. As is apparent from FIGS. 5 and 6, temples 30 cannot be removed from front 12 without aligning the cutouts in apertures 26 and 28 with tabs 32a and 34a on pins 32 and 34. Preferably, the cutouts in apertures 26 and 28 are so disposed that such alignment occurs with the temples 30 folded; this minimizes the chance that the temples 30 will become separated when worn in their unfolded, rearwardly extending position.

Referring particularly to FIGS. 3 to 5, each of the front portions 40 of temples 30 is formed with an upper channel 48 and a lower channel 50 recessed inwardly (i.e., toward the vertical plane VP of FIG. 2) relative to the unrecessed portions of front wall portion 40. Recessed portions or channels 48 and 50 have respective portions 52 and 54 that extend forwardly of the plane a—a defined by the rear edges of the front 12 so as to overlap the adjacent portions of front 12 as shown in FIGS. 3 and 4. Preferably, the depth of the recessed portions 48 and 50 is greatest at the front and gradually decreases toward the rear of the temple 30. Although the front portion 40 of each temple 30 is generally recessed, the unrecessed temple portions, including upper portion 56, middle portion 58 between recesses 48 and 50 and lower portion 60, mate with the rear edges of side portions 20 of front 12 to define an outer limit position for pivotal movement of the temples 30 relative to the front 12.

Recesses 48 and 50 direct air flow from the ambient region between the forwardly extending portions 52 and 54 and the adjacent side portions 20 of front 12 against the rear surface of the central portion 16. Owing to the overlap between forwardly extending portions 52 and 54 and the adjacent side portions 20 of front 12, the chance of injury due to projectiles or the like is greatly reduced.

It will be seen that we have accomplished the objects of our invention. Our safety spectacles adequately protect the wearer from injury, while at the same time affording adequate ventilation and resisting fogging. Our spectacles are also simple and inexpensive to manufacture. It will be understood that certain features and subcombinations are of utility and may be employed without reference to other features and subcombinations. This is contemplated by and is within the scope of our claims. It is further obvious that various changes may be made in details within the scope of our claims without departing from the spirit of our invention. It is, therefore, to be understood that our invention is not to be limited to the specific details shown and described.

Having thus described our invention, what we claim is:

1. Safety spectacles including in combination a central front having a left side and a right side, each side and having a rear edge, a left temple and a right temple, each temple extending rearwardly and having a portion abutting the rear edge of a corresponding side, each temple having a recess, each recess having a forward edge spaced inwardly of the abutting portion of the temple, each recess extending rearwardly and outwardly, and means for pivotly attaching each temple to a corresponding side, said recesses directing air forwardly and the said abutting portion providing angular stops limiting pivotal movement of the temples relative to the sides.

2. Spectacles as in claim 1 wherein each temple comprises a pair of discrete abutting portions vertically separated by the recess and respectively disposed at the top and at the bottom.

3. Spectacles as in claim 1 wherein each recess forms an inner wall of a forwardly extending passageway having an outer wall, each recess extending forwards and overlapping the outer wall of the passageway sufficiently to shield an eye from injury.

4. Spectacles as in claim 1 wherein each temple comprises a pair of discrete abutting portions vertically separated by the recess.

5. Spectacles as in claim 1 wherein each temple comprises three discrete abutting portions vertically separated by and alternating with two recesses.

6. Spectacles as in claim 1 wherein each recess at its forward edge and the corresponding side at its rear edge extend substantially parallel to one another, said recesses directing air substantially tangentially to the inside surfaces of the sides.

7. Spectacles as in claim 1 wherein each side has a curved inside portion which turns directed air inwardly along the inside surface of the front.

8. Spectacles as in claim 1 wherein each side is curved and turns directed air inwardly along the inside surface of the front.

9. Spectacles as in claim 1 wherein each recess forms an inner wall of a forwardly extending passageway having a substantially outer wall, each recess extending forwards and overlapping the outer wall of the passageway sufficiently to direct air substantially tangentially to the inside surfaces of the sides.

Reconsideration of the application as amended is respectively requested.

* * * * *

UNITED STATES PATENT AND TRADEMARK OFFICE
CERTIFICATE OF CORRECTION

PATENT NO. : 4,964,714

DATED : October 23, 1990

INVENTOR(S) : Russell F. Weymouth, Jr., John J. McNamara, Joseph A. Cianflone

It is certified that error appears in the above-identified patent and that said Letters Patent is hereby corrected as shown below:

Column 4, line 56 - delete "and" (first occurrence).

line 64 - "portion" should read -- portions --.

Column 6, line 11 - after "substantially" insert -- parallel --.

lines 15 and 16 - delete "Reconsideration of the application as amended is respectively requested".

Signed and Sealed this

Seventeenth Day of March, 1992

*Attest:*

HARRY F. MANBECK, JR.

*Attesting Officer*       *Commissioner of Patents and Trademarks*